United States Patent [19]

Fyffe

[11] Patent Number: 5,421,721
[45] Date of Patent: Jun. 6, 1995

[54] DENTAL FORCEPS

[76] Inventor: David Fyffe, 10018 Lawler, Dallas, Tex. 75243

[21] Appl. No.: 868,623

[22] Filed: Apr. 14, 1992

[51] Int. Cl.[6] .......................... A61C 3/14; A61C 3/16; B25B 7/02
[52] U.S. Cl. ........................................ 433/159; 81/421
[58] Field of Search ................... 433/157, 158, 159, 4; 81/420, 421

[56] References Cited

U.S. PATENT DOCUMENTS

| | | | |
|---|---|---|---|
| 732,288 | 6/1903 | Felsch | 433/159 |
| 1,395,714 | 11/1921 | Johnson | 433/159 |
| 1,653,803 | 12/1927 | Fisher | 81/421 |
| 1,730,230 | 10/1929 | Miller | 433/159 |
| 2,679,775 | 6/1954 | Fleming | 81/420 |

Primary Examiner—Nicholas D. Lucchesi
Attorney, Agent, or Firm—David G. Henry

[57] ABSTRACT

The invention prescribes forceps for dental use, one embodiment of which exhibits an enclosure for trapping extracted teeth and dental appliances so as to prevent them, when slipping from the grasp of the forceps' beaks, from falling into the mouth or throat of a patient. A second embodiment includes an abutment member lying inward from the beaks against which abutment member an extracted tooth or dental appliance is lodged as occlusions of the beaks forces the tooth or appliance inward from the beak tips.

3 Claims, 4 Drawing Sheets

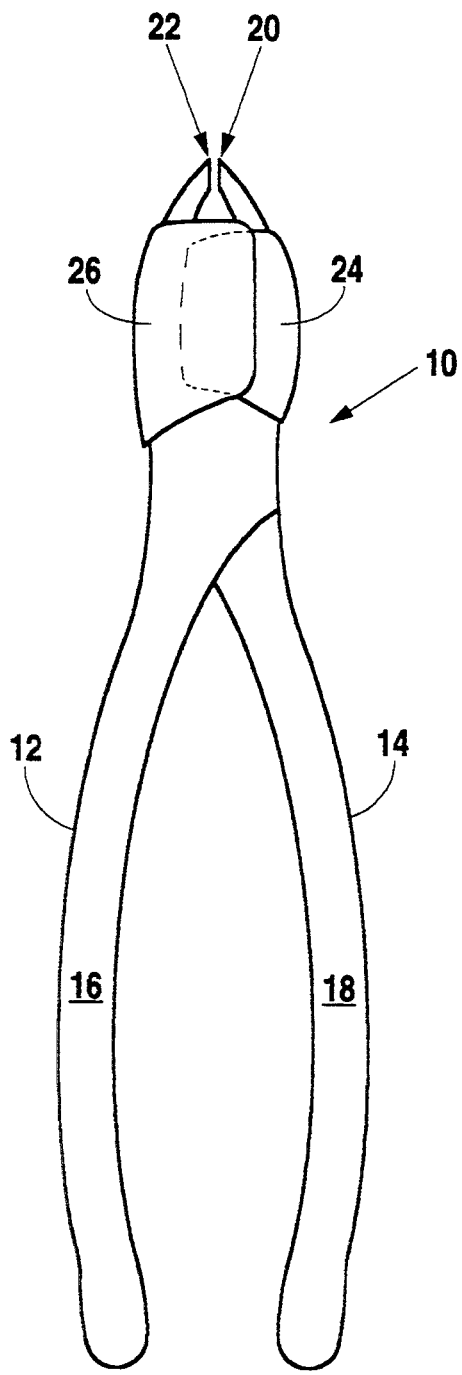
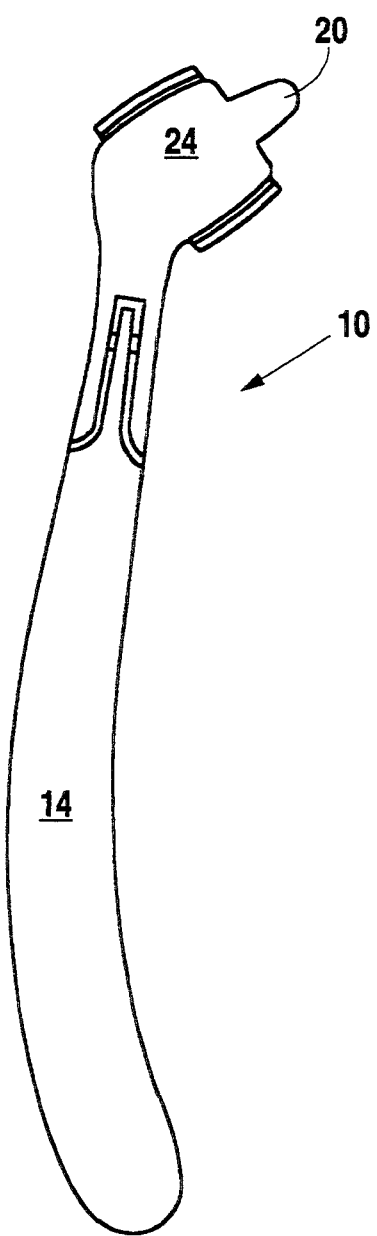
Fig. 3
Fig. 4

DENTAL FORCEPS

BACKGROUND OF THE INVENTION

1. Field of The Invention

Applicant's invention relates to dental instruments.

2. Background Information

Forceps are the instruments used by dentists to extract teeth and dental appliances. Forceps slippage is a common problem among dentists and dental specialists.

Slippage of teeth and dental appliances from their respective dental instruments can occur in all of the following situations: (1) removal of short-rooted, bell-shaped teeth; (2) removal of temporary crowns; (3) removal of orthodontic brackets; and (4) removal of primary teeth.

When an extracted tooth or dental appliance slips from a forceps' beaks, swallowing or aspirating the tooth or appliance can occur. This can translate into in potentially life-threatening medical situation.

Referring to FIGS. 1 and 2, a problem of particular concern is the difficulty of grasping (gripping) primary or baby teeth 110. In most instances, primary teeth 110 have resorbed (dissolved, non-existent) roots leaving the crown portion of the tooth loosely connected to a gum tissue ridge 112. During extraction of primary teeth 112 using forceps 118, slippage of the forceps tip 116 below the apical (bottom) edge 114 of the tooth 112 is common. With further squeezing of the handle of the forceps 118, the direction of motion of the tooth 112 is in an occlusal or incisal direction (a direction up and away from the gums.) The tooth 112 then falls out the sides of the forceps beaks and into the mouth of the patient. Such teeth 112 also have a tendency to "pop" off of the forceps beaks 116 and fly surprisingly long distances.

Forceps are not presently well enough designed with respect to size or configuration to allow for such slippage problems while maintaining control of an extracted tooth or dental appliance. This is because current forceps design is limited to a very small number of sizes and tip (beak) contours. Such a "one-size-fits all" approach by the dental instrument industry yields forceps which do not adequately grasp teeth and dental appliances with their widely varying sizes and shapes.

The cost to dental instrument companies and practitioners for respectively making and purchasing an adequate array of differently sized and shaped forceps for reducing the likelihood of slippage is prohibitive. Regardless of the cost, such an investment would far from completely eliminate the chance that loose, extracted teeth and dental appliances will pose the above-described dangers to patients.

Accordingly, any practical approach to the problem of forceps slippage is one which seeks to mitigate the potential complications from forceps slippage, rather than unrealistically trying to avoid slippage altogether.

To date, no known dental instrument reflects such an approach. The phenomena of forceps slippage obviously presents health risks to patients, particularly pedodontic patients who a not likely able to respond to instructions in properly dealing with the occurrence. In addition, however, the practitioner is presented with potential legal risks. Despite the best of skills and caution, injury to a child from a swallowed or aspirated tooth will almost certainly give rise to a lawsuit (or at least an expensive and time-consuming out-of-court settlement). Accordingly, it is imperative that the problem of loose extracted teeth and dental appliances be addressed at once.

SUMMARY OF THE INVENTION

In light of the foregoing, it is an object of the present invention to provide a dental instrument useful for extracting teeth and dental appliances and improved with respect to safety of the patient.

It is an object of the present invention to provide a novel dental instrument which serves to extract teeth and dental appliances and to thereafter capture the same.

It is another object of the present invention to provide a novel dental instrument which reduces the likelihood of injury to a patient resulting from extracted teeth or dental appliances falling into the patient's mount or throat.

It is another object of the present invention to provide an improved dental forceps which incorporates a mechanism for enveloping and immobilizing an extracted tooth or dental appliance.

It is yet another object of the present invention to provide improved dental forceps which obstruct the natural exit path of an extracted tooth or dental appliance so as to prevent the tooth or appliance from falling into the patient's mouth or throat and from exiting the patients mouth.

In satisfaction of these and related objectives, Applicant's present invention provides two improved forceps designs, both of which address the problems which accompany forceps slippage upon extraction of teeth and dental appliances.

A first design incorporates an enclosure for capturing extracted teeth and dental appliances upon extraction. The enclosure is defined by two shrouds which overlie the forceps beaks and which cooperate to define an enclosure with an opening therein which widens when the forceps beaks are opened for grasping a tooth or dental appliance and constricts when the forceps beaks meet underneath an extracted tooth or appliance.

A second forceps design prescribes a rod which is positioned medial to the beak tips of the forceps and serves as a stop against which an extracted tooth or dental appliance is lodged to prevent its falling into or being propelled from a patients mouth.

The devices of Applicant's invention permit their users to extract teeth and dental appliances with substantially less probability that injury or liability will follow the inevitable forceps slippage. When (not if) a tooth or appliance slips from the grasp of the forceps' beaks, it will (depending on which of Applicant's designs are used) either be captured in an enclosure or lodged against an abutment rod.

BRIEF DESCRIPTION OF THE DRAWINGS

FIG. 3 is an elevational front view of a preferred embodiment of Applicant's invention.

FIG. 4 is an elevational side view of the forceps of FIG. 3.

DETAILED DESCRIPTION OF THE PREFERRED EMBODIMENT

Figure 1:
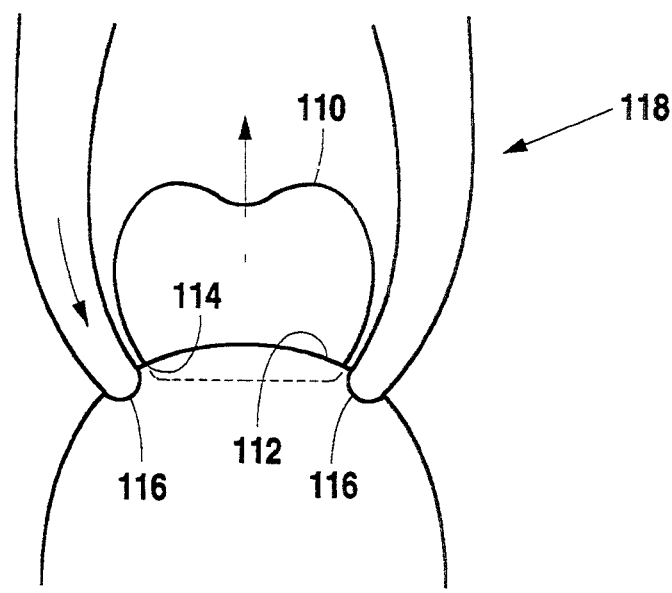
FIG. 1 is an elevational end view of a tooth, at the gum line, being extracted with standard dental forceps.
Figure 2:
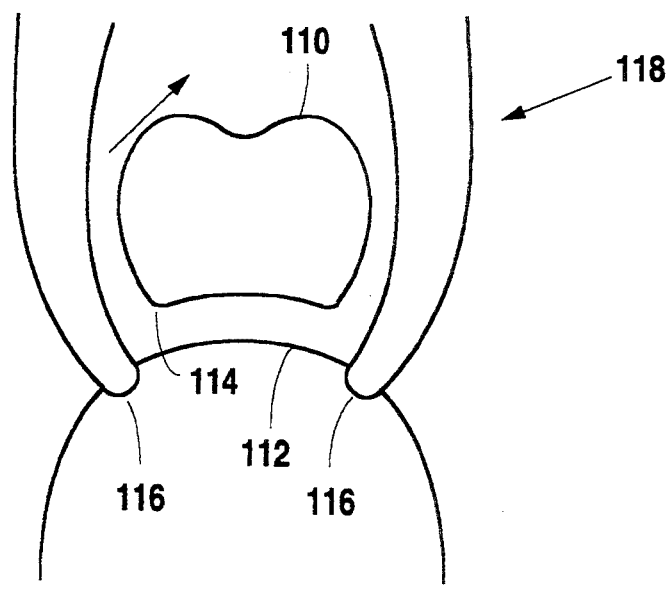
FIG. 2 is an elevational end view of an extracted tooth having slipped from between the beaks of standard dental forceps.

Referring to FIG. 3, one preferred embodiment of Applicant's invention is depicted generally by the reference numeral 10. As with any dental forceps, forceps 10 includes a first forceps tong 12 and a second forceps tong 14. Tongs 12 and 14 and hingedly mated in a plier-like configuration. Tongs 12 and 14 respectively exhibit handle portions 16 and 18 as well as beaks 20 and 22.

Unlike any other known dental forceps, forceps 10 include shrouds 24 and 26 which are respectively formed near the beak ends of tongs 12 and 14.

Figure 5:
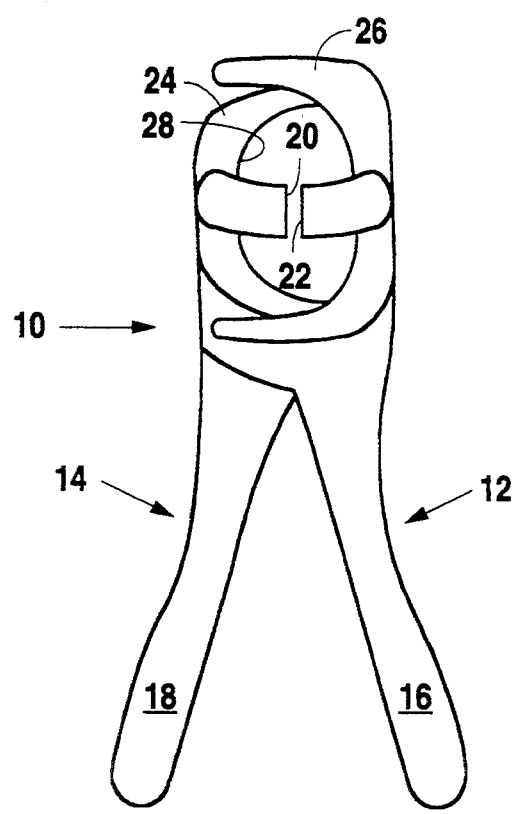
FIG. 5 is a perspective view of the beak end of the forceps of FIG. 3 with the beaks in their apposed configuration.
Figure 6:
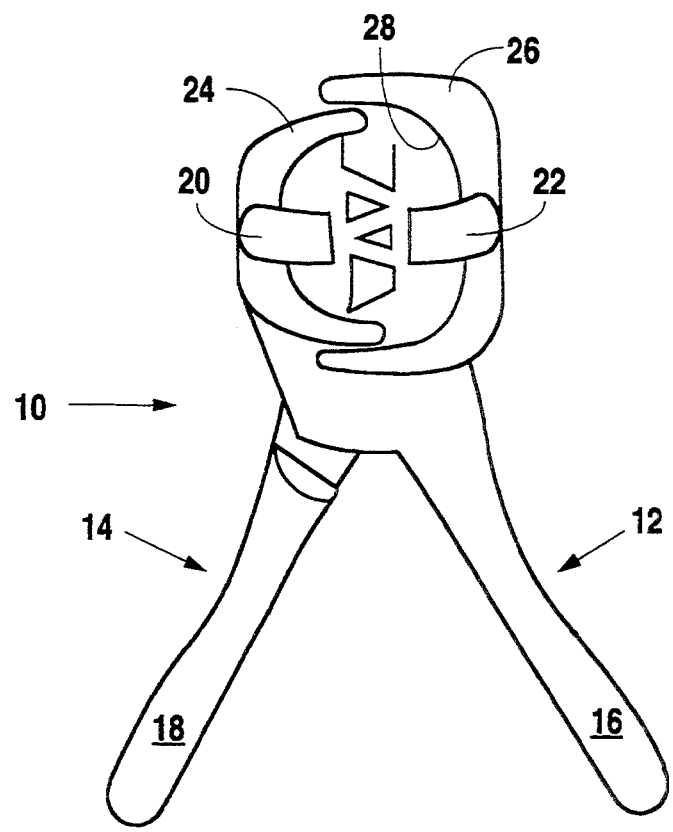
FIG. 6 is a perspective view of the beak end of the forceps of FIG. 3 with the beaks in their open configuration.

Referring particularly to FIGS. 3, 5 and 6, shrouds 24 and 26 and complimentarily shaped and sized whereby shroud 24 partially nests within shroud 26 as the tongs 12 and 14 are moved to their beak-apposing position (FIG. 5). When the tongs 12 and 14 are moved toward their expanded-beak configuration (FIG. 6), shroud 24 moves partially from the interior confines of shroud 26.

As is clear from FIGS. 5 and 6, shrouds 24 and 26 cooperatively define an enclosure which lies in a medial or handle direction from the beaks 20 and 22 as well as an orifice 28 which opens into the enclosure adjacent to the beaks 20 and 22. The orifice 28 expands and constricts respectively as the tongs are moved between their beak-apposing and expanded beak positions. In this manner, an extracted tooth or dental appliance is most likely to be trapped within the enclosure as the beaks close after extracting the tooth or appliance.

It should be noted that visualization of a to-be extracted tooth or dental appliance may be hindered by the shrouds 24 and 26, Accordingly, one alternative embodiment of Applicant's invention (not shown in the drawings) includes perforated shrouds. These shrouds exhibit a number of holes formed in the metal forming the shroud, each hole being sized smaller than any dimension of a small, but normal primary tooth. Still another embodiment includes a screen-like metal fabric which is formed into shrouds for defining an enclosure which is operatively equivalent to that depicted in the drawings.

The shape and orientation of beaks 20 and 22 should be substantially like those of forceps in the prior art. The forceps 10 should be formed of surgical stainless steel as is customary in the industry.

Figure 7:
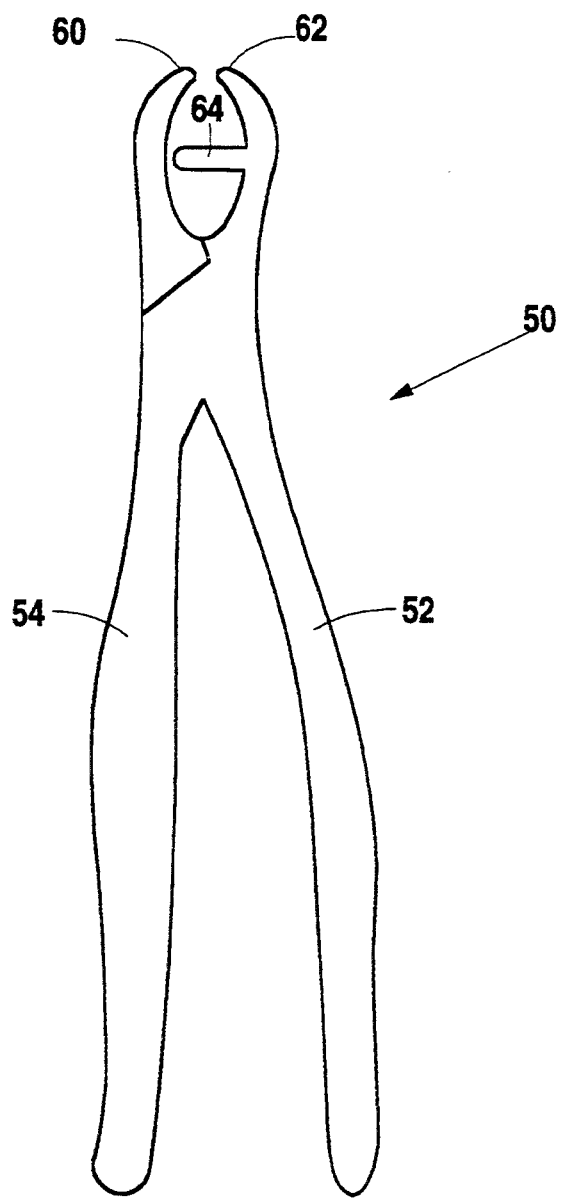
FIG. 7 is an elevational front view of a second embodiment of Applicant's invention.

Referring to FIG. 7, a second embodiment of Applicant's invention is depicted—forceps 50. Forceps 50 exhibit a first forceps tong 52 and a second forceps tong 54. Tongs 52 and 54 and hingedly mated in a plier-like configuration just as with tongs 12 and 14 of forceps 10. Tongs 52 and 54 respectively exhibit beaks 60 and 62.

Figure 8:
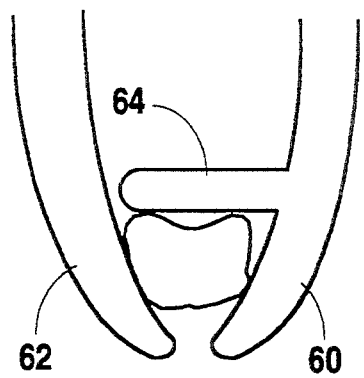
FIG. 8 is an elevational view of the beak end of the forceps of FIG. 7 with an extracted tooth shown captured therein.

Referring more specifically to FIG. 8, the beak end portion of forceps 50 is shown. Unlike forceps 10, forceps 50 lack shrouds, but instead exhibit an abutment member 64 which extends from tong 54 near beak 62 as shown in FIG. 8. Complimenting abutment member 64 is a abutment recess (not visible in the drawings) which receives abutment member 64 when the tongs 60 and 62 move to a beak-apposed configuration.

As shown in FIG. 8, once a tooth is extracted and has moved in a handle direction from the beak tips, the tooth becomes trapped in the triangular like space jointly defined by the interior surfaces of the beaks 60 and 62 and the abutment member 64.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An apparatus for dental work comprising:

first and second forceps tongs hingedly mated in a plier-like assemblage for moving between a first beak-apposed configuration and a second expanded-beak configuration;

each said tong having a handle portion at a handle end and a beak at a beak end, said beaks of said first and second tongs being positioned and oriented for operably juxtaposing when said tongs are moved to said first beak-apposed configuration, said first tong further exhibiting a first shroud member positioned adjacent to and in a handle direction from said beak of said first tong, said second tong further exhibiting a second shroud member positioned adjacent to and in a handle direction from said beak of said second tong, said first shroud member and said second shroud member cooperatively defining an enclosure with an orifice thereinto being defined adjacent to said beaks;

said shrouds being formed from perforated material.

2. The invention of claim 1 wherein said first shroud member is sized and shaped for partially nesting within said second shroud member when said tongs move toward said first beak-apposed configuration and wherein said orifice is constricted when said tongs move toward said first beak-apposed configuration.

3. Dental forceps comprising:

a first tong having a first handle end and a first beak end, with a first beak being formed at said first beak end and with a first enclosure member, exhibiting an orifice thereinto, being formed adjacent to said first beak; and a second tong having a second handle end and a second beak end, with a second beak being formed at said second beak end and a second enclosure member which, cooperative with said first enclosure member defines an enclosure and said orifice;

said first and second beaks being positioned and oriented relative to each other and to said orifice of said enclosure members whereby a tooth extracted by action of said first and second beaks and passing in a handle direction from said beaks will enter said enclosure by way of said orifice;

said first enclosure member being configured in a telescopic nesting arrangement with said second enclosure member whereby when said first and second tongs move with respect to each other, said first and second enclosure members move between first and second extreme nesting degrees and said orifice changes in size between largest and smallest dimensions.

* * * * *